US008503747B2

(12) United States Patent
Park et al.

(10) Patent No.: US 8,503,747 B2
(45) Date of Patent: Aug. 6, 2013

(54) IMAGE ANALYSIS FOR CERVICAL NEOPLASIA DETECTION AND DIAGNOSIS

(75) Inventors: Sun Young Park, San Diego, CA (US); Dustin Sargent, San Diego, CA (US); Ulf Peter Gustafsson, San Diego, CA (US)

(73) Assignee: STI Medical Systems, LLC, La Jolla, CA (US)

( * ) Notice: Subject to any disclaimer, the term of this patent is extended or adjusted under 35 U.S.C. 154(b) by 275 days.

(21) Appl. No.: 13/068,188

(22) Filed: May 3, 2011

(65) Prior Publication Data

US 2011/0274338 A1 Nov. 10, 2011

Related U.S. Application Data

(60) Provisional application No. 61/343,757, filed on May 3, 2010.

(51) Int. Cl.

*G06K 9/00* (2006.01)
*A61B 6/00* (2006.01)

(52) U.S. Cl.

USPC .............................. 382/128; 382/224; 378/18

(58) Field of Classification Search

USPC ................. 382/100, 106–107, 128–134, 162, 382/168, 173, 181, 189–190, 203, 219, 224, 382/232, 254, 274, 276, 305, 312; 345/634; 348/46; 378/18, 21

See application file for complete search history.

(56) References Cited

U.S. PATENT DOCUMENTS

| | | | | |
|---|---|---|---|---|
| 7,664,300 | B2 * | 2/2010 | Lange et al. | 382/128 |
| 2008/0226147 | A1 * | 9/2008 | Hargrove et al. | 382/128 |
| 2008/0226148 | A1 * | 9/2008 | Gu et al. | 382/128 |
| 2009/0034824 | A1 * | 2/2009 | Li et al. | 382/133 |
| 2010/0033501 | A1 * | 2/2010 | Whitesell et al. | 345/634 |
| 2010/0149315 | A1 * | 6/2010 | Qu et al. | 348/46 |

* cited by examiner

*Primary Examiner* — Seyed Azarian
(74) *Attorney, Agent, or Firm* — Martin E. Hsia

(57) ABSTRACT

The present invention is an automated image analysis framework for cervical cancerous lesion detection. The present invention uses domain-specific diagnostic features in a probabilistic manner using conditional random fields. In addition, the present invention discloses a novel window-based performance assessment scheme for two-dimensional image analysis, which addresses the intrinsic problem of image misalignment. As a domain-specific anatomical feature, image regions corresponding to different tissue types are extracted from cervical images taken before and after the application of acetic acid during a clinical exam. The unique optical properties of each tissue type and the diagnostic relationships between neighboring regions are incorporated in the conditional random field model. The output provides information about both the tissue severity and the location of cancerous tissue in an image.

6 Claims, 12 Drawing Sheets

IMAGE ANALYSIS FOR CERVICAL NEOPLASIA DETECTION AND DIAGNOSIS

This application claims the priority of U.S. provisional patent application No. 61/343,757, filed on May 3, 2010.

TECHNICAL FIELD

The present invention generally relates to medical imaging, and more specifically to an automated image analysis framework for the detection and diagnosis of cervical cancerous lesions.

BACKGROUND ART

Although this invention is being disclosed in connection with cervical cancer, it is applicable to many other areas of medicine. Cervical cancer is preventable with early detection but still comprises approximately 12% of all cancer cases in women worldwide (World Health Organization, "Global Health Risks", December 2009, incorporated herein by reference). This considerable number of cervical cancer cases is mainly attributed to the lack of cervical cancer prevention programs in developing countries. Even though cervical cancer prevention programs such as the Papanicolaou (Pap) smear have been effective in reducing the incidence and mortality of cervical cancer, developing countries often lack the sophisticated laboratory equipment, highly trained personnel and financial resources necessary to implement these programs (R. Sankaranarayanan, A. M. Budukh, and R. Rajkumar, "Effective screening programmes for cervical cancer in low- and middle-income developing countries," *Bulletin of the World Health Organization* 79, pp. 954-962, 2001; H. S. Cronje, "Screening for cervical cancer in developing countries," *International Journal of Gynecology and Obstetrics* 84(2), pp. 101-108, 2004; and A. Batson, F. Meheus, and S. Brooke, "Chapter 26: Innovative financing mechanisms to accelerate the introduction of HPV vaccines in developing countries," *Vaccine* 24, pp. 219-225, 2006; incorporated herein by reference). Without a cost effective cervical cancer screening solution, cervical cancer remains a leading cause of cancer-related death among women in developing countries.

To address this problem, alternative cost effective cervical cancer screening methods have been investigated (L. Denny, L. Kuhn, A. Pollack, H. Wainwright, and T. Wright, "Evaluation of alternative methods of cervical cancer screening for resource-poor settings," *Cancer* 89(4), pp. 826-833, 2000; T. C. Wright Jr, M. Menton, J. F. Myrtle, C. Chow, and A. Singer, "Visualization techniques (colposcopy, direct visual inspection, and spectroscopic and other visual methods). Summary of task force 7," *Acta Cytologica* 46(5), pp. 793-800, 2002; J. Benavides, S. Chang, S. Park, R. Richards-Kortum, N. MacKinnon, C. MacAulay, A. Milbourne, A. Malpica, and M. Follen, "Multispectral digital colposcopy for in vivo detection of cervical cancer," *Optics Express* 11(10), pp. 1223-1236, 2003; S. J. Goldie, L. Gaffikin, J. D. Goldhaber-Fiebert, A. Gordillo-Tobar, C. Levin, C. Mahe, and T. C. Wright, "Cost-effectiveness of cervical-cancer screening in five developing countries," *The New England Journal of Medicine* 353(20), p. 2158, 2005; J. Jeronimo, O. Morales, J. Horna, J. Pariona, J. Manrique, J. Rubi?s, and R. Takahashi, "Visual inspection with acetic acid for cervical cancer screening outside of low-resource settings," *Revista panamericana de salud publica* 17, pp. 1-5, 2005; D. Roblyer, S. Y. Park, R. Richards-Kortum, I. Adewole, and M. Follen, "Objective screening for cervical cancer in developing nations: Lessons from Nigeria," *Gynecologic Oncology* 107(1S), pp. 94-97, 2007; S. Y. Park, M. Follen, A. Milbourne, H. Rhodes, A. Malpica, N. MacKinnon, C. MacAulay, M. K. Markey, and R. Richards-Kortum, "Automated image analysis of digital colposcopy for the detection of cervical neoplasia," *Journal of Biomedical Optics* 13, p. 014029, 2008; and N. Thekkek and R. Richards-Kortum, "Optical imaging for cervical cancer detection: solutions for a continuing global problem," *Nature Reviews. Cancer* 8(9), p. 725, 2008, incorporated herein by reference) and considerable efforts have been devoted to digital colposcopy with automated image analysis techniques (W. E. Crisp, B. L. Craine, and E. A. Craine, "The computerized digital imaging colposcope: future directions," *American Journal of Obstetrics and Gynecology* 162(6), p. 1491, 1990; B. L. Craine and E. R. Craine, "Digital imaging colposcopy: basic concepts and applications," *Obstetrics & Gynecology* 82(5), p. 869, 1993; M. I. Shafi, J. A. Dunn, R. Chenoy, E. J. Buxton, C. Williams, and D. M. Luesley, "Digital imaging colposcopy, image analysis and quantification of the colposcopic image," *British Journal of Obstetrics and Gynaecology* 101(3), p. 234, 1994; P. M. Cristoforoni, D. Gerbaldo, A. Perino, R. Piccoli, F. J. Montz, and G. L. Capitanio, "Computerized colposcopy: Results of a pilot study and analysis of its clinical relevance," *Obstetrics and Gynecology* 85, p. 1011, 1995; Q. Ji, J. Engel, and E. Craine, "Texture analysis for classification of cervix lesions," *IEEE Transactions on Medical Imaging* 19(11), pp. 1144-1149, 2000; E. D. Dickman, T. J. Doll, C. K. Chiu, and D. G. Ferris, "Identification of cervical neoplasia using a simulation of human vision," *Journal of Lower Genital Tract Disease* 5(3), p. 144, 2001; S. Gordon, G. Zimmerman, and H. Greenspan, "Image segmentation of uterine cervix images for indexing in PACS," *Proc. of 17th IEEE Symposium on Computer-Based Medical Systems*, pp. 298-303, 2004; A. Milbourne, S. Y. Park, J. L. Benedet, D. Miller, T. Ehlen, H. Rhodes, A. Malpica, J. Matisic, D. Van Niekirk, and E. N. Atkinson; "Results of a pilot study of multispectral digital colposcopy for the in vivo detection of cervical intraepithelial neoplasia," *Gynecologic Oncology* 99(3S), pp. 67-75, 2005; S. Gordon, G. Zimmerman, R. Long, S. Antani, J. Jeronimo, and H. Greenspan, "Content analysis of uterine cervix images: initial steps towards content based indexing and retrieval of cervigrams," *Proc. of SPIE Medical Imaging* 6144, pp. 1549-1556, 2006; W. Li and A. Poirson, "Detection and characterization of abnormal vascular patterns in automated cervical image analysis," *Lecture Notes in Computer Science* 4292, p. 627, 2006; W. Li, J. Gu, D. Ferris, and A. Poirson, "Automated image analysis of uterine cervical images," *Proc. of SPIE Medical Imaging* 6514. pp. 65142P-1 (2007); S. Y. Park, "A study on diagnostic image analysis for the detection of precancerous lesions using multispectral digital images," PhD Thesis University of Texas at Austin, 2007; S. Y. Park, M. Follen, A. Milbourne, H. Rhodes, A. Malpica, N. MacKinnon, C. MacAulay, M. K. Markey, and R. Richards-Kortum, "Automated image analysis of digital colposcopy for the detection of cervical neoplasia," *Journal of Biomedical Optics* 13, p. 014029, 2008; W. Li, S. Venkataraman, U. Gustafsson, J. C. Oyama, D. G. Ferris, and R. W. Lieberman, "Using acetowhite opacity index for detecting cervical intraepithelial neoplasia," *Journal of Biomedical Optics, vol.* 14, p. 014020, 2009; and H. G. Acosta-Mesa, N. Cruz-Ramirez and R. Hermandez-Jimenez, "Aceto-white temporal pattern classification using k-NN to identify precancerous cervical lesion in colposcopic images," *Computers in Biology and Medicine,* 39(9), pp. 778-784, 2009, incorporated herein with reference).

Many studies have shown that digital colposcopy with image-based diagnosis of cancer and pre-cancer has the potential to improve, or even replace, conventional colposcopy. The consistent and accurate diagnoses provided by digital image analysis have the potential to allow less experienced physicians to provide a standard of care on par with expert colposcopists. In the early 1990s, several studies showed the feasibility of using digital image processing techniques to automatically interpret colposcopic images (W. E. Crisp, B. L. Craine, and E. A. Craine, "The computerized digital imaging colposcope: future directions," *American Journal of Obstetrics and Gynecology* 162(6), p. 1491, 1990; B. L. Craine and E. R. Craine, "Digital imaging colposcopy: basic concepts and applications," *Obstetrics & Gynecology* 82(5), p. 869, 1993; M. I. Shafi, J. A. Dunn, R. Chenoy, E. J. Buxton, C. Williams, and D. M. Luesley, "Digital imaging colposcopy, image analysis and quantification of the colposcopic image," *British Journal of Obstetrics and Gynaecology* 101(3), p. 234, 1994; and P. M. Cristoforoni, D. Gerbaldo, A. Perino, R. Piccoli, F. J. Montz, and G. L. Capitanio, "Computerized colposcopy: Results of a pilot study and analysis of its clinical relevance," *Obstetrics and Gynecology* 85, p. 1011, 1995, incorporated herein by reference). In these early studies, diagnostic image interpretation relied primarily on qualitative image assessment from expert colposcopists and provided limited quantitative analysis.

Since these early proof-of-principle reports, automated algorithms have been designed with the goal of minimizing the need for provider (physician) intervention (E. D. Dickman, T. J. Doll, C. K. Chiu, and D. G. Ferris, "Identification of cervical neoplasia using a simulation of human vision,"*Journal of Lower Genital Tract Disease* 5(3), p. 144, 2001; S. Gordon, G. Zimmerman, and H. Greenspan, "Image segmentation of uterine cervix images for indexing in PACS," *Proc. of* 17*th IEEE Symposium on Computer-Based Medical Systems, pp.* 298-303, 2004; A. Milbourne, S. Y. Park, J. L. Benedet, D. Miller, T. Ehlen, H. Rhodes, A. Malpica, J. Matisic, D. Van Niekirk, and E. N. Atkinson, "Results of a pilot study of multispectral digital colposcopy for the in vivo detection of cervical intraepithelial neoplasia," *Gynecologic Oncology* 99(3S), pp. 67-75, 2005; S. Gordon, G. Zimmerman, R. Long, S. Antani, J. Jeronimo, and H. Greenspan, "Content analysis of uterine cervix images: initial steps towards content based indexing and retrieval of cervigrams," *Proc. of SPIE Medical Imaging* 6144, pp. 1549-1556, 2006; W. Li, J. Gu, D. Ferris, and A. Poirson, "Automated image analysis of uterine cervical images," *Proc. of SPIE* 6514, pp. 65142P-, 2007; S. Y. Park, "A study on diagnostic image analysis for the detection of precancerous lesions using multispectral digital images," PhD Thesis University of Texas at Austin, 2007; S. Y. Park, M. Follen, A. Milbourne, H. Rhodes, A. Malpica, N. MacKinnon, C. MacAulay, M. K. Markey, and R. Richards-Kortum, "Automated image analysis of digital colposcopy for the detection of cervical neoplasia," *Journal of Biomedical Optics* 13, p. 014029, 2008; W. Li, S. Venkataraman, U. Gustafsson, J. C. Oyama, D. G. Ferris, and R. W. Lieberman, "Using acetowhite opacity index for detecting cervical intraepithelial neoplasia," *Journal of Biomedical Optics* 14, p. 014020, 2009; H. G. Acosta-Mesa, N. Cruz-Ramirez and R. Hermandez-Jimenez, "Aceto-white temporal pattern classification using k-NN to identify precancerous cervical lesion in colposcopic images," *Computers in Biology and Medicine,* 39(9), pp. 778-784, 2009; W. Li, R. W. Lieberman, S. Nie, Y. Xie, M. Eldred, and J. Oyama, "Histopathology reconstruction on digital imagery," *Proc. of SPIE Medical Imaging* 7263, p. 726303, 2009, incorporated herein by reference).

Dickman et al. (E. D. Dickman, T. J. Doll, C. K. Chiu, and D. G. Ferris, "Identification of cervical neoplasia using a simulation of human vision," *Journal of Lower Genital Tract Disease* 5(3), p. 144, 2001, incorporated herein by reference) investigated the detection of cervical cancer and precursors from cervix images using a computer simulation of human vision. They trained a vision system to recognize normal and abnormal cervical images, and demonstrated 100% sensitivity and 98% specificity in detecting CIN3 on a very small data set of 8 images only.

Gordon and Li (S. Gordon, G. Zimmerman, and H. Greenspan, "Image segmentation of uterine cervix images for indexing in PACS," *Proc. of* 17*th IEEE Symposium on Computer-Based Medical Systems, pp.* 298-303, 2004; S. Gordon, G. Zimmerman, R. Long, S. Antani, J. Jeronimo, and H. Greenspan, "Content analysis of uterine cervix images: initial steps towards content based indexing and retrieval of cervigrams," *Proc. of SPIE Medical Imaging* 6144, pp. 1549-1556, 2006; and W. Li, J. Gu, D. Ferris, and A. Poirson, "Automated image analysis of uterine cervical images," *Proc. of SPIE Medical Imaging* 6514, p. 65142P-1, 2007, incorporated herein by reference) developed image analysis algorithms to segment the anatomical regions of the cervix, such as the columnar epithelium, the squamous epithelium, the endocervical canal, and the transformation zone, based on color intensity values. Their research showed that a potential for accurate segmentation of the cervical anatomy exists. However, their work did not incorporate spatial relationships between tissue types and other diagnostic features, and they did not report the diagnostic accuracy of their algorithm.

Li et al. (W. Li, S. Venkataraman, U. Gustafsson, J. C. Oyama, D. G. Ferris, and R. W. Lieberman, "Using acetowhite opacity index for detecting cervical intraepithelial neoplasia," *Journal of Biomedical Optics* 14, p. 014020, 2009, incorporated herein by reference) designed a computer-aided diagnostic system using an acetowhitening opacity index with a reported patient-based diagnostic result of 88% sensitivity and 84% specificity.

Similarly, Park et al (S. Y. Park, "A study on diagnostic image analysis for the detection of precancerous lesions using multispectral digital images," PhD Thesis University of Texas at Austin, 2007; and S. Y. Park, M. Follen, A. Milbourne, H. Rhodes, A. Malpica, N. MacKinnon, C. MacAulay, M. K. Markey, and R. Richards-Kortum, "Automated image analysis of digital colposcopy for the detection of cervical neoplasia," *Journal of Biomedical Optics* 13, p. 014029, 2008, incorporated herein by reference) designed a diagnostic image analysis framework using acetowhitening-based statistical features, reporting both patient-based and image-based diagnostic performances. The results showed 79% sensitivity and 88% specificity for the patient-based approach, and 82% sensitivity and 73% specificity for the image-based approach.

These currently reported diagnostic algorithms, however, have not fully taken advantage of cervical biology. Instead, the techniques have been generic rather than domain-specific, and have not been tailored to utilize the unique optical features of specific tissue, in this case, cervical tissue. The diagnostic performance of image analysis may be significantly enhanced by incorporating cervical cancer-specific (domain-specific) features in the algorithm design. For example, it is known that cervical cancer is mainly caused by the infection of metaplastic epithelium in the cervical transformation zone with one or more carcinogenic types of human papillomavirus (HPV) (D. A. Elson, R. R. Riley, A. Lacey, G. Thordarson, F. J. Talamantes, and J. M. Arbeit, "Sensitivity of the cervical transformation zone to estrogen-induced squamous carcinogenesis," *Cancer Research* 60(5), p. 1267, 2000, incorporated herein by reference). In addition, some reports (see for example I. M. Orfanoudaki, G. C. Themelis, S. K. Sifakis, D.

H. Fragouli, J. G. Panayiotides, E. M. Vazgiouraki, and E. E. Koumantakis, “A clinical study of optical biopsy of the uterine cervix using a multispectral imaging system,” Gynecologic Oncology 96(1), pp. 119-131, 2005; and J. Mirkovic, C. Lau, S. McGee, C. C. Yu, J. Nazemi, L. Galindo, V. Feng, T. Darragh, A. de Las Morenas, and C. Crum, “Effect of anatomy on spectroscopic detection of cervical dysplasia,” *Journal of Biomedical Optics* 14, p. 044021, 2009, incorporated herein by reference) have shown that differences in tissue structure between tissue types yield different optical properties for each tissue type. It has also been reported that the columnar tissue in the transformation zone of the cervix is spectroscopically distinct from the adjacent squamous tissue, and that these anatomical differences directly influence the spectroscopic diagnostic parameters (J. Mirkovic, C. Lau, S. McGee, C. C. Yu, J. Nazemi, L. Galindo, V. Feng, T. Darragh, A. de Las Morenas, and C. Crum, “Effect of anatomy on spectroscopic detection of cervical dysplasia,” *Journal of Biomedical Optics* 14, p. 044021, 2009, incorporated herein by reference). Furthermore, one study has shown that acetowhite response curves have different decays in the squamous tissue, the columnar tissue and the transformation zone (I. M. Orfanoudaki, G. C. Themelis, S. K. Sifakis, D. H. Fragouli, J. G. Panayiotides, E. M. Vazgiouraki, and E. E. Koumantakis, “A clinical study of optical biopsy of the uterine cervix using a multispectral imaging system,” *Gynecologic Oncology* 96(1), pp. 119-131, 2005, incorporated herein by reference). These studies and reports suggest that the performance of cervical cancer detection algorithms can be improved by incorporating tissue type information.

Previously reported methods also have not considered the spatial relationships between diagnostic features. For example, as taught in colposcopy textbooks (see B. S. Apgar, Brotzman, G. L. and Spitzer, M., “Colposcopy: Principles and Practice”, W.B. Saunders Company, Philadelphia, 2002, incorporated herein by reference), the presence of both acetowhitening and mosaicism indicates a high probability of cervical neoplasia (cervical cancer or an abnormal proliferation of cells in the cervix). These relationships between the features in a cervical image provide diagnostically valuable information in addition to that provided by the features themselves.

Most of the previous studies also lack image-based diagnostic performance assessment methods. Some of the studies used patient-based sensitivity and specificity. A patient-based performance analysis measures the algorithm’s ability to accurately make positive and negative cancer predictions for each patient. However, patient-based performance analysis does not assess an algorithm’s ability to correctly locate the image region containing cancerous tissue (abnormal area). If abnormal areas can be accurately located, the size of the surgical excision can be reduced, which in turn reduces the patient’s discomfort. Likewise, accurate detection of the abnormal area can help pinpoint locations for biopsies. Therefore, a sound diagnostic performance measure for automated image analysis should assess an algorithm’s ability not just to diagnose a patient, but also to locate the abnormal area.

The following patents and patent applications may be considered relevant to the field of the invention:

U.S. Pat. No. 6,236,881 to Zahler et al., incorporated herein by reference, discloses a computerized apparatus with a real time detection algorithm for non drug-activated imaging diseases, for example in cervical and bladder tissues.

U.S. Pat. No. 6,766,184 to Utzinger et al., incorporated herein by reference, discloses methods and apparatus for generating multispectral images of tissue. The multispectral images may be used as a diagnostic tool for conditions such as cervical cancer detection and diagnosis. Apparatus utilizing the invention include endoscopes and colposcopes.

U.S. Pat. No. 6,933,154 to Schomacker et al., incorporated herein by reference, provides methods for determining a characteristic of a tissue sample, such as a state of health, using spectral data and/or images obtained within an optimal period of time following the application of a chemical agent to the tissue sample.

U.S. Pat. No. 7,187,810 to Clune et al., incorporated herein by reference, provides methods of determining a correction for a misalignment between at least two images in a sequence of images due at least in part to sample movement. The methods are applied, for example, in the processing and analysis of a sequence of images of biological tissue in a diagnostic procedure. The invention also provides methods of validating the correction for a misalignment between at least two images in a sequence of images of a sample. The methods may be applied in deciding whether a correction for misalignment accurately accounts for sample motion.

U.S. Pat. No. 7,664,300 to Lange et al., incorporated herein by reference, discloses a uterine cervical cancer computer-aided-diagnosis (CAD) system consisting of a core processing system that automatically analyses data acquired from the uterine cervix and provides tissue and patient diagnosis, as well as adequacy of the examination.

U.S. Patent Application No. 2006/0039593 to Sammak et al., incorporated herein by reference, discloses methods and systems for determining characteristics of cellular structures. The methods include non-invasive, non-perturbing, automatable, and quantitative methods and may be applied to the examination of cells such as stem cells, embryos, and egg cells.

U.S. Patent Application Publication No. 2008/0039720 to Balas, incorporated herein by reference, discloses a quantitative method for determining tissue characteristics including the steps of generating data for a dynamic optical curve over a period of time based on an optical property of a tissue and determining a value of a dynamic optical parameter. The value of the dynamic optical parameter is compared with a reference value of the dynamic optical parameter known to be linked to a structural or functional characteristic and/or the pathological status of the tissue. Based on the comparison, a structural or functional characteristic and/or the pathological status of the tissue is determined. The method is used diagnose and/or grade neoplasia and/or HPV infection and/or calculating nuclear to cytoplasmic ratios of the cells in the tissue sample.

U.S. Patent Application Publication No. 2008/0101678 to Suliga et al., incorporated herein by reference, describes a Markov Random Field (MRF) based technique for performing clustering of images characterized by poor or limited data. The proposed method is a statistical classification model that labels image pixels based on the description of their statistical and contextual information. Apart from evaluating the pixel statistics that originate from the definition of the K-means clustering scheme, the model expands the analysis by the description of the spatial dependence between pixels and their labels (context), leading to the reduction of the inhomogeneity of the segmentation output with respect to the result of pure K-means clustering.

U.S. Patent Application Publication No. 2009/0034824 to Li et al., incorporated herein by reference, discloses a method for differentiating cancerous lesions from surrounding tissue, which includes extracting an opacity parameter from acetowhite regions of pre-acetic acid and post-acetic acid images of a cervix.

U.S. Patent Application Publication No. 2009/0253991 to Balas et al., incorporated herein by reference, discloses a method and an apparatus for the in vivo, non-invasive, early detection of alterations and mapping of the grade of these alterations, causing in the biochemical and/or in the functional characteristics of the epithelial tissues, during the development of tissue, atypias, dysplasias, neoplasias and cancers.

U.S. Patent Application Publication No. 2010/0027863 to Venkataraman et al., incorporated herein by reference, discloses a method for the detection of atypical vessels in digital cervical imagery.

U.S. Patent Application Publication No. 2010/0092064 to Li et al., incorporated herein by reference, discloses a rule-based unsupervised process for classifying cervical tissue by serially applying classifiers selected from the group comprising of determining size of texture region, opacity parameter, size of acetowhite regions, number of coarse and fine punctations, size of coarse and fine mosaics, size of atypical blood vessels and demographic data, so that the cervical tissue can be classified into no evidence of disease, low-grade dysplasia, high-grade dysplasia or cancer.

DISCLOSURE OF THE INVENTION

The present invention discloses a novel automated domain-specific image analysis method for cervical neoplasia detection which addresses the shortcomings of previous studies, reports, and developments:

First, features specific to cervical tissue (domain-specific features) are utilized at every stage of the proposed method, from pre-processing and image segmentation to the final classification stage. The design is based on two important clinical observations: (1) most cervical pre-cancers or cancers occur at the transformation zone of the uterine cervix (A. Stall and R. F. Mattingly, "Colposcopic diagnosis of cervical neoplasia," *Obstetrics & Gynecology* 41(2), p. 168, 1973, incorporated herein by reference); and (2) the optical properties of tissue vary as a function of the tissue type. The present invention uses an anatomical feature map to incorporate the knowledge that cervical pre-cancer mainly arises in the cervical transformation zone.

Second, diagnostic features related with tissue types and their spatial relationships are utilized using a cervical image analysis framework based on the theory of Conditional Random Field (CRF) (see for example J. Lafferty, A. McCallum, and F. Pereira, "Conditional random fields: Probabilistic models for segmenting and labeling sequence data," in Machine Learning-International Workshop, 282-289, 2001; and H. Greenspan, S. Peled, S., G. Oz, and N. Kiryati, "MRI Inter-slice Reconstruction using Super-resolution," *Lecture Notes in Computer Science Medical Image Computation and Computer-Assisted Intervention—MICCAI* 2001 2208, pp. 1204-1206, 2008, incorporated herein by reference). CRF is a probabilistic framework used for labeling and segmenting structured data by defining a conditional probability distribution over label sequences given a particular observation sequence, rather than a joint distribution over both label and observation sequences. In the present invention, the so-called Markov property of the CRF probabilistically models the diagnostic relationships between neighboring tissues and different tissue types. The CRF model also characterizes the spreading behavior of cancer cells to neighboring tissues. Further, the CRF model used in the present invention is able to simultaneously accommodate multiple cervical cancer imaging modalities, such as fluorescence and narrow-band images, without modification. Also without modification, the present invention is able to analyze information from any number of images in a time-course acetowhitening decay sequence.

Third, the present invention incorporates statistical features related to both acetowhitening and vessel structure. Previous approaches have used only acetowhitening features. The use of acetowhitening and vessel features takes advantage of previously reported relationships, such as the fact that the presence of both acetowhitening and mosaicism indicates a high probability of cervical neoplasia.

Finally, in order to locate abnormal areas in cervical images, the present invention discloses a window-based performance evaluation based on sensitivity and specificity measures. The stability of the method to locate abnormal image regions is compared with expert colposcopy annotations, using histopathology as the ground truth. To the best of the inventor's knowledge and belief, this is the first reported method to explicitly measure an algorithm's ability to locate abnormal image regions.

Accordingly, the present invention comprises a process for detection and diagnosis of cancer in tissues, comprising acquiring polarized and non-polarized images of the tissues, normalizing the images to account for color and spatial variations, registering the images to correct for tissue deformation, generating an anatomical features map from the images using color and texture information, identifying regions in the images of different tissue types based on the anatomical features map (so that each region has only one tissue type), segmenting sub-regions within each region that are homogeneous in color and intensity, extracting diagnostically relevant features from each of the sub-regions (where the diagnostically relevant features are selected from the group consisting of acetowhitening and abnormal blood vessel features) and classifying the sub-regions as normal or abnormal based on said extracted diagnostically relevant features in the sub-regions and probabilistic dependencies based on classification of neighboring regions.

The present invention also comprises extracting diagnostically relevant features step for acetowhitening by calculating mean, standard deviation, entropy and ratios between different color channels of pre-acetic acid images and post-acetic acid images.

The present invention also comprises extracting abnormal vessel features by applying a linear rotating structuring element and a morphological transformation to automatically detect mosaicism, punctation, and atypical vessel patterns by extracting intercapillary distance between vessels, size of each vessel, and density of vessels.

The present invention further comprises automatically classifying tissues in each sub-region as normal or abnormal using a conditional random field classifier that incorporates probabilistic dependencies on classification of neighboring sub-regions.

The present invention is preferably practiced where the tissues are cervical tissues and the identifying step identifies said tissue types as squamous epithelium, columnar epithelium, cervical os, and transformation zone.

The present invention is preferably practiced where the images are red, green and blue visible light images.

The images can be pre-acetic acid images, post-acetic acid images, time course acetowhite images and reflectance and fluorescence images.

The disclosed diagnostic approach has the potential to support or substitute for conventional colposcopy. The design is also capable of accepting as input any number and type of images. For cervical cancer applications in particular, the input may include pre-acetic and post-acetic images, time-course acetowhite decay images, as well as fluorescence images in any number and combination. These additional images and modalities integrate naturally into the proposed embodiments of the current invention without requiring any modification. Further, the generalized framework can be applied to other cancers, including but not limited to skin, oral and colon cancer.

BRIEF DESCRIPTION OF THE DRAWINGS

FIG. 7(*b*) illustrates a histopathology slide between points A to B in FIG. 7(*a*). The inserts display magnified portions of the tissue surface exhibiting significantly different tissue structures.

FIGS. 10(*b*) and 11(*b*) show the colposcopy annotations performed by an expert colposcopist. The subject in FIG. 11(*b*) was deemed normal by the colposcopist resulting in no colposcopy annotations.

FIGS. 10(*c*) and 11(*c*) shows the result of the present invention.

BEST MODE FOR CARRYING OUT THE INVENTION

Figure 1:
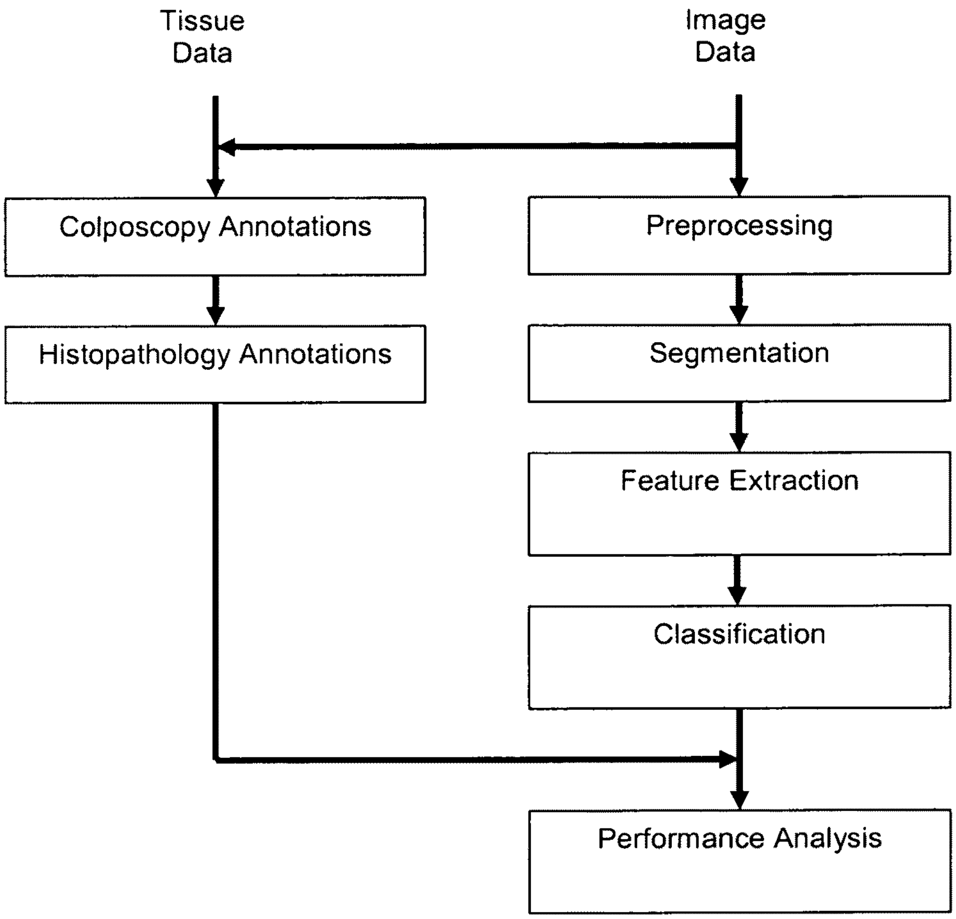
FIG. 1 illustrates the automated image analysis framework for cervical cancer detection and diagnosis with tissue and image input data, colposcopy and histopathology annotations, and analysis steps of image preprocessing, image segmentation, diagnostic feature extraction, diagnostic image classification, and performance analysis.

The presently preferred embodiment of the invention presented herein discloses an automated image analysis framework, schematically illustrated in FIG. 1, for cervical cancer detection and diagnosis. The framework uses high-resolution instrumentation to acquire high quality, clinical cervical image data, as well as tissue data in the form of colposcopy and histopatology annotations. The diagnostic image analysis framework is comprised of a series of image analysis steps in which image preprocessing, image segmentation, diagnostic feature extraction and diagnostic image assessment are applied in sequential order. In the final step, a performance analysis of the diagnostic image analysis output is applied.

Instrumentation and Data

Instrumentation

The image data used in the development of the cervical cancer detection and diagnosis framework were acquired with a digital imaging device designed specifically for the acquisition of cervical images and subsequent optical analysis by a colposcopist.

In one preferred embodiment of the invention, the digital imaging device consists of an modified optical colposcope (for example, Seiler, Series 935) to include two high-resolution 14 Megapixels RGB color digital cameras (for example, Kodak, DCS Pro SLR/n) and a fiber guided light source assembly (for example, Perkin Elmer, DiX1765 Xenon lamp). The modified colposcope enables stereoscopic imaging capabilities (three-dimensional image reconstruction) and the acquisition of non-polarized and polarized reflectance imagery (but other types of images can be used, including, but not limited to, fluorescence images). The non-polarized imagery is susceptible to specular reflection (glint), which saturates all signals and can cause problems in extracting diagnostic information from the affected areas. The polarized imagery minimizes glint at the expense of a slight decrease in resolution. Using a high resolution digital colposcope allows computer programs to detect colposcopically important features (see for example D. G. Ferris, J. T. Cox, D. M. O'Connor, V. C. Wright, and J. Foerster, *Modern Colposcopy. Textbook and Atlas*, pp. 1-699, American Society for Colposcopy and Cervical Pathology, 2004, incorporated herein by reference), including but not limited to acetowhite, lesion borders, fine and coarse mosaic, punctuation and atypical blood vessels. It also allows computer programs to assess and determine the size of lesions, features, and inter-capillary distances.

Further, in another preferred embodiment of the invention, a high resolution digital video colposcope with built-in polarized light emitting illumination can be used (as described in a co-pending, commonly assigned U.S. patent application Ser. No. 12/291,890 for "High resolution digital video colposcope with built in polarized LED illumination and computerized clinical data management system", filed Aug. 1, 2008, incorporated herein by reference).

Data

The clinical reflectance image data used for the present invention was acquired from women with cervical cytologic abnormalities and a concordant colposcopic diagnosis, who were all scheduled for a LEEP conducted at hospitals in Lima and Cusco, Peru, and in Augusta, Ga. The study protocol was reviewed and approved by the institutional review boards (IRB) at the clinical sites. Eligible patients were females between 22 and 50 years old, were not pregnant, were without cervical hemorrhage, and were referred to the colposcopy clinic with an abnormal Papanicolaou (PAP) smear for a LEEP. All participants read and signed an IRB approved informed consent document.

Following a colposcopic examination, but prior to the application of 5% acetic acid (which enhances the contrast between normal and acetic acid responsive tissue areas), polarized white-light reflectance images as well as non-polarized reflectance images are acquired from each patient (these images are hereafter referred to as "pre-acetic acid images"). One minute after the acetic acid application, sequential polarized and non-polarized images are acquired every 10 seconds for five minutes (these images are hereafter referred to as "post-acetic acid images"). The female subjects then undergo a LEEP procedure following the application of Lugol's iodine solution and subcutaneous administration of an anesthetic and a vasoconstrictive agent.

After the clinical exam, colposcopic features including the ectocervix, external os, columnar epithelium, squamous epithelium, acetowhite epithelium, mosaicism, punctation, atypical vessels and lesion margins are annotated on a post-acetic acid image by the study expert colposcopist. The LEEP specimens are processed and areas of cervical intraepithelial neoplasia (CIN) are annotated on the histopathology slide images by an expert histopathologist. These histopathology annotations are used as ground truth in the performance evaluation.

In order to maintain the spatial orientation of the LEEP specimens relative to the area of excision during histopathology processing and correlate the CIN areas back to the acquired cervical reflectance images, the LEEP specimens are preferably processed and analyzed according to a method described in a co-pending, commonly assigned U.S. patent application Ser. No. 12/587,614 for "Process for preserving 3D orientation to allow registering histopathological diagnoses of tissue to images of that tissue," filed Oct. 9, 2008, incorporated herein by reference.

Diagnostic Image Analysis

Image Preprocessing

The preferred embodiment of the present invention contains three sequential steps for image preprocessing. The first preprocessing step, image calibration, normalizes the cervical reflectance images to account for color and spatial variations caused by differences in lighting conditions and camera settings between images. This first step preferably uses the method described in a co-pending, commonly assigned U.S. patent application Ser. No. 12/077,659 for "Method of Automated Image Color Calibration", filed Mar. 17, 2007, incorporated herein by reference.

The second preprocessing step is image registration, which corrects for tissue deformation between two images obtained before and after the application of acetic acid. In order to correct for tissue deformation induced by the application of acetic acid, an elastic image registration method using nonlinear optimization is preferably used (as described in J. D. Arteaga, J. Kybic, and W. Li, "Elastic image registration for movement compensation in digital colposcopy," *BIOSIGNAL: Analysis of Biomedical Signals and Images*, Brno, Czech Republic, 2006, incorporated herein by reference).

Figure 2:
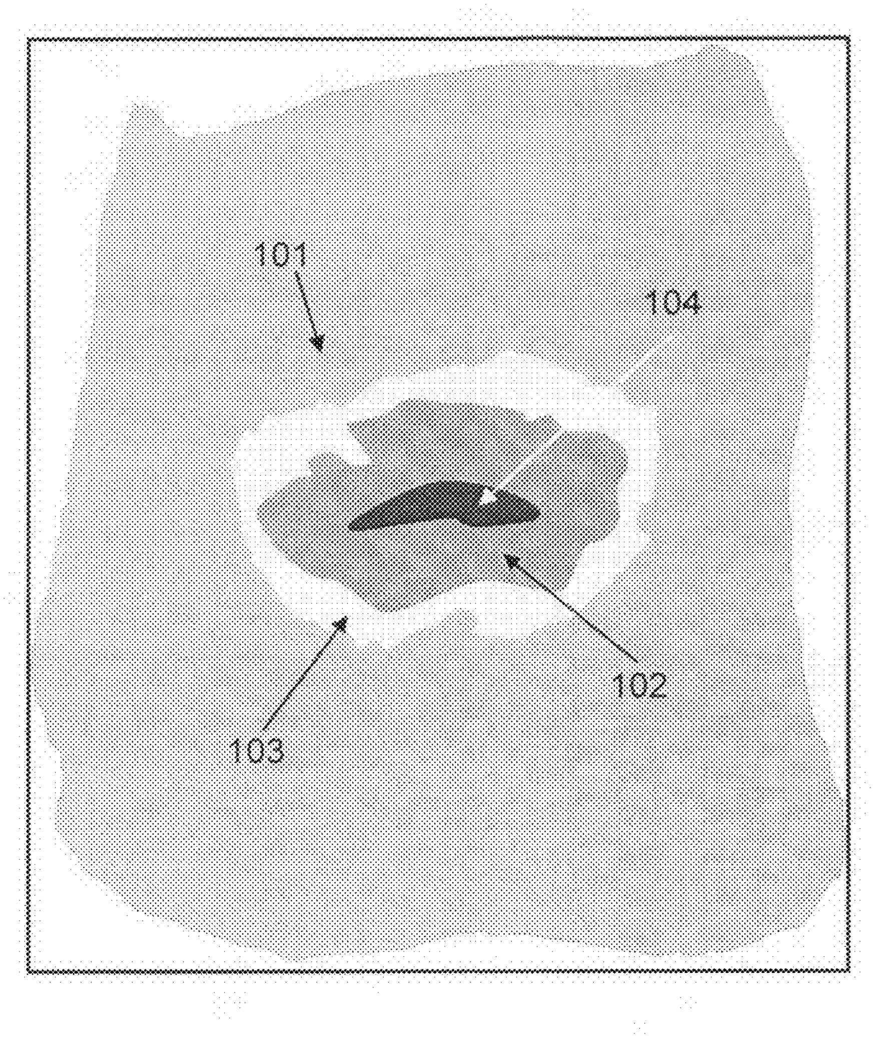
FIG. 2 illustrates the anatomical features of squamous (101) and columnar (102) epithelium, transformation zone (103) and cervical os (104) of a cervix.

The final preprocessing step, anatomical feature extraction, identifies the regions of different tissue types in the pre- and post-acetic acid cervical reflectance images. Using color and texture information, the algorithm generates an anatomical feature map (a two-dimensional map indicating the locations of the squamous and columnar epithelium, the transformation zone and the cervical os) as illustrated in FIG. 2 and as described in S. Y. Park, M. Follen, A. Milbourne, H. Rhodes, A. Malpica, N. MacKinnon, C. MacAulay, M. K. Markey, and R. Richards-Kortum, "Automated image analysis of digital colposcopy for the detection of cervical neoplasia," *Journal of Biomedical Optics* 13, p. 014029, 2008; and S. Y. Park, "A study on diagnostic image analysis for the detection of precancerous lesions using multispectral digital images." PhD Thesis University of Texas at Austin, 2007, incorporated herein by reference.

Squamous and columnar epithelium are extracted based on color information. For cervical tissue (see FIG. 2), squamous epithelium (101) appears pinkish and columnar epithelium (102) appears reddish. An expectation-maximization (EM) algorithm is used for non-parametric estimation of the two color distributions.

The cervical os (104) is a small, low intensity area located in the center of the cervix and surrounded by the columnar epithelium (102) and the transformation zone (103). The size and shape of the cervical os (104) varies with age, hormones, and vaginal birth state. In the present invention, the cervical os (104) is automatically detected using an adaptive threshold with an eigenvalue decomposition method (as described in K. Etemad and R. Chellapa, "Face recognition using discriminant eigenvectors," *IEEE International Conference on Acoustics, Speech, and Signal Processing ICASSP*-96, 2148-2151, 1996, incorporated herein by reference).

The transformation zone (103) is the area in which abnormal growths and changes in the cells are most often found. It is located between the squamous (101) and columnar epitheliums (102) and is the site of squamous metaplasia (the reversible replacement of one differentiated cell type with another mature differentiated cell type). An intensity gradient map is used to characterize changes in tissue texture, and the transformation zone (103) is identified as a region of high variation.

The anatomical feature maps are used to both analyze the optical properties of different tissue types and to design the other diagnostic image analysis algorithms, including image segmentation and CRF-based diagnostic image classification (as further detailed in the following sections).

Image Segmentation

The anatomical feature map generated during the preprocessing step is preferably used to perform image segmentation for each cervical tissue type separately. This means that the tissue regions defined by the anatomical feature map are further clustered into sub-regions. The boundaries defined by the anatomical feature map ensure that these sub-regions each contain only one type of tissue. A region-based, rather than pixel-based, classification is used because it is more robust to intrinsic registration errors that remain even after the extraction of the anatomical feature map.

The region-based approach is also used because of the observation that changes in color and intensity in cervical images correlate closely with changes in tissue type, severity of cervical neoplasia and vessel patterns. These changes are of crucial importance for diagnostic classification. Therefore, the goal of image segmentation of the present invention is to identify sub-regions within each tissue type that are homogeneous in color and intensity. To achieve this goal, the preferred embodiment of the invention preferably utilizes a new image segmentation algorithm based on K-means clustering (N. Otsu, "A threshold selection method from gray level histograms", *IEEE Transactions on Systems, Man, and Cybernetics* 9(1), 62-66, 1979, incorporated herein by reference).

In designing this new segmentation algorithm, it was first determined whether image segmentation using pixel intensity features alone would be sufficient to describe the anatomical structures in cervical images. This segmentation refers to segmentation of the image as a whole, without first using the anatomical feature map to subdivide the image into different tissue type regions. For this test, the intensities and ratios of the intensities of the different color channels of the camera system are extracted. Using an RGB color camera for the cervical image data collection, ten features were extracted: the intensities of the red, green, and blue channels, and the green to red and blue to red intensity ratios of the polarized pre-acetic acid and post-acetic acid cervical reflectance images. For other camera systems, acquiring data in other color modes than RGB, such as CMYK (cyan, magenta, yellow, and key (black)), other ratios can be generated.

Furthermore, to integrate the relative contributions of these features for segmentation, each feature was weighted by its Shannon entropy function (C. E. Shannon, "A mathematical theory of communication," *ACM SIGMOBILE Mobile Computing and Communications Review* 5(1), 3-55, 2001, incorporated herein by reference) defined by $$H(A)=-\Sigma p(a)\log_2 p(a), \quad (1)$$

where A is a random variable representing the intensity feature, a is a realization of A, and p(●) is the probability mass function of A.

This weighting approach prioritizes the features that vary significantly throughout the image, and thus provide the most information for image segmentation. The preferred approach is directly related to information gain (T. Mitchell, Machine learning McGraw Hill, 1997, incorporated herein by reference) and is a common feature weighting method in classification (P. S. Kostka, E. J. Tkacz, and D. Komorowski, "Hybrid feature vector extraction in unsupervised learning neural classifier," *IEEE Annual International Conference of the Engineering in Medicine and Biology Society IEEE-EMBS* 2005, pp. 5664-5667, 2006, incorporated herein by reference) and in feature selection (A. Abbasi, H. Chen, and J. P. Salenius, "Sentiment analysis in multiple languages: Feature selection for opinion classification in Web forums," *ACM Transactions on Information Systems* (*TOIS*) 26(3), 2008, incorporated herein by reference).

Figure 3A:
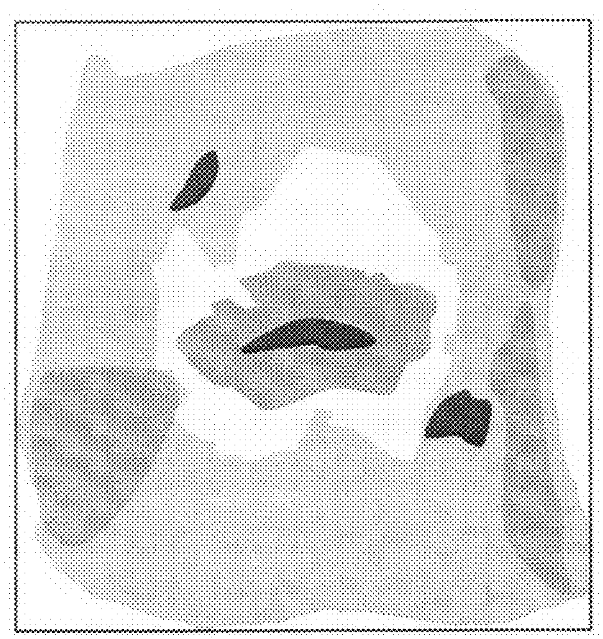
FIG. 3(*a*) illustrates clustering results with image information, and FIG. 3(*b*) illustrates clustering results without image information.
Figure 3B:
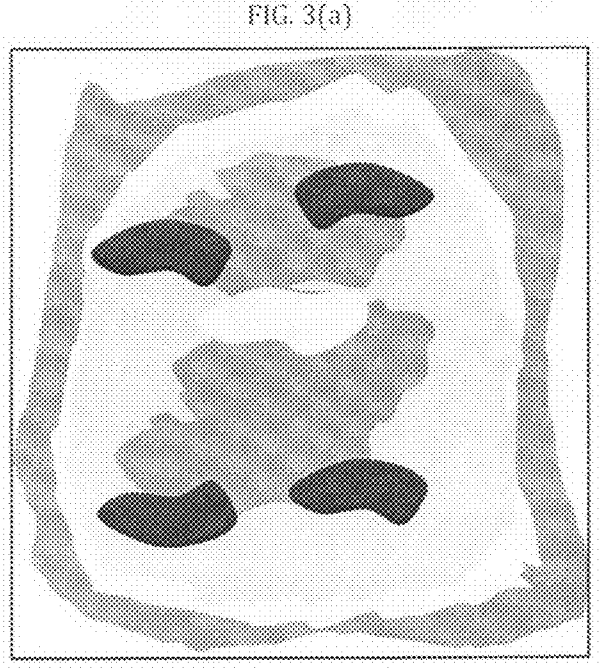

FIG. 3 illustrates the segmentation results for two cervical images. FIG. 3(*a*) shows the segmentation results using tissue information, while FIG. 3(*b*) shows segmentations of the same image without using image information. Comparisons between FIG. 3(*a*) and (*b*) qualitatively suggest that incorporating tissue information provides additional information for diagnostically meaningful segmentation.

Thus, the resulting image regions without tissue information (FIG. 3(*a*) and (*c*)) do not correspond well to the anatomical structures of the cervix. To address this problem, the new segmentation approach of the present invention uses the anatomical feature maps generated during the preprocessing step to explicitly incorporate anatomical features into the segmentation algorithm. This means that the image region for each tissue type is identified based on the anatomical feature map, and the algorithm performs segmentations for each tissue type separately. This way, the resulting segmented image regions do not contain multiple tissue types and they correspond well to the anatomical structures of the cervix (as illustrated in FIGS. 3(*b*) and (*d*)).

To quantitatively determine the impact of using tissue type information in image segmentation a clustering performance measure is applied (as described by D. Davies and D. Bouldin, "A cluster separation measure," *IEEE Transactions on Pattern Analysis and Machine Intelligence* 10, 224-227, 1973, incorporated herein by reference). This method starts by calculating the within-cluster inertia $W_k$ for cluster k according to $$W_k = \frac{1}{n_k}\sum_{i\in C_k} d(x_i^k, x_c^k) \quad (2)$$

where $x_c^k$ is the center of the cluster k, $n_k$ is the number of points in the cluster k, $d(x_i^k, x_c^k)$ represents a distance between two points $x_i^k$ and $x_c^k$, and $C_k$ is the set of points belonging to the cluster k. A between-cluster inertia function $B_{jk}$k for the clusters j and k is also calculated according to $$B_{jk}=d(x_c^k,x_c^j). \quad (3)$$

Then, the Davies-Bouldin (DB) index $\lambda^{DB}$ is defined according to $$\lambda^{DB} = \frac{1}{K}\sum_{k=1}^{K} R_k, \quad (4)$$

where $$R_k = \max_{j\neq k}\left\{\frac{W_k + W_j}{B_{kj}}\right\} \quad (5)$$

and K is the number of clusters. Using the DB index, the better performing segmentation algorithm is identified by a higher DB index value (meaning that it yields clusters with smaller intra-cluster distances and larger inter-cluster distances).

Figure 4:
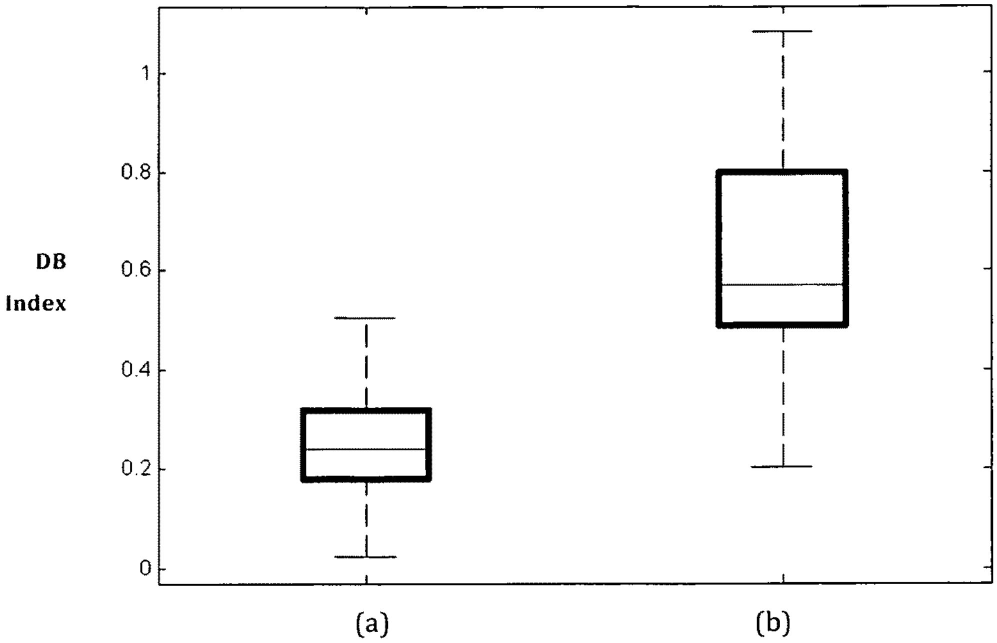
FIG. 4(*a*) shows box plots of the Davies-Bouldin (DB) index of the clustering results with tissue information, and FIG. 4(*b*) shows box plots of the DB index of the clustering results without tissue information.

To compare the performance of the two segmentation methods FIG. 4 shows box plots of the DB index without (FIG. 4(*a*)) and with (FIG. 4(*b*)) tissue information. FIG. 4 clearly shows a higher DB index by including the tissue information and, thus, provides improved segmentation performance.

Diagnostic Feature Extraction

Figure 5:
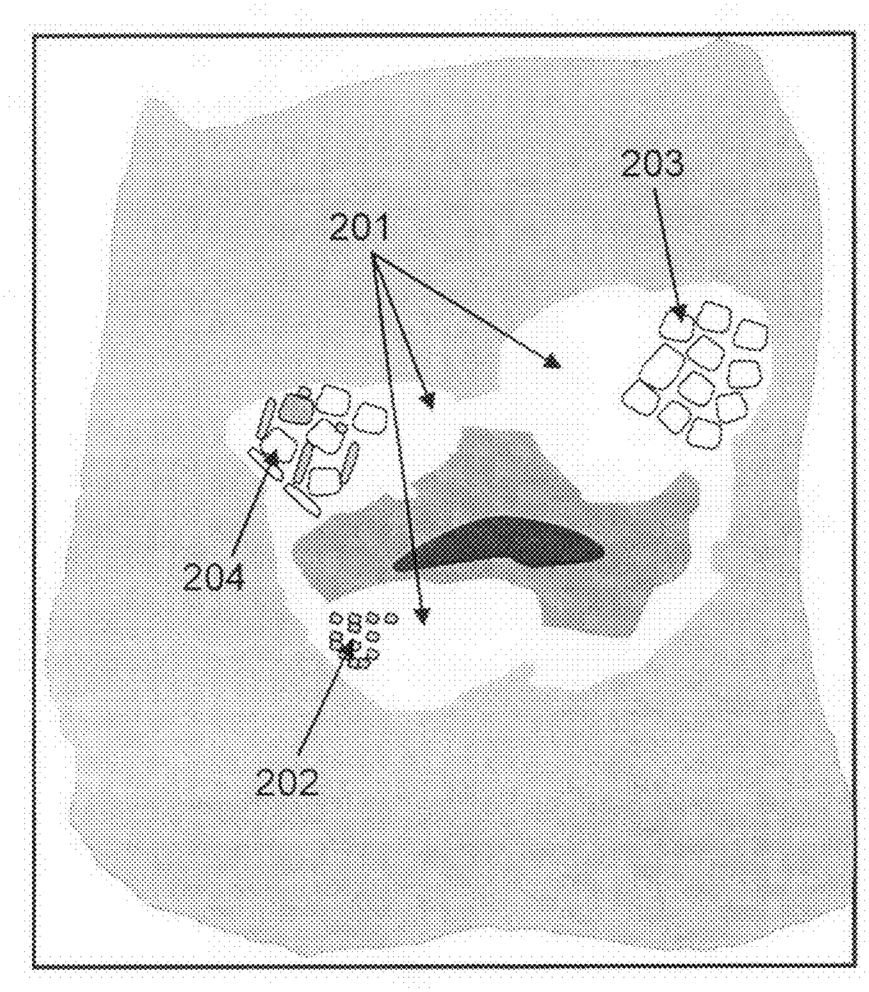
FIG. 5 illustrates the diagnostically relevant features of acetowhitening (201), punctation (202), mosaic (203), and atypical vessels (204).

Once the cervical reflectance images have been segmented, diagnostically relevant features including but not limited to acetowhitening, mosaicism, punctation, and atypical vessels are preferably extracted from each image region. FIG. 5 illustrates these features.

The degree of acetowhitening varies depending on the severity of cervical neoplasia. The acetowhite features are extracted from the segmented image regions for the pre-acetic acid images and post-acetic acid images and from the intensity difference images between pre-acetic acid images and post-acetic acid images. The statistical measures of the mean, standard deviation and entropy are calculated, as are the ratios between the different color channels of the cervical RGB images.

Abnormal vessel features, such as punctations, mosaics and atypical vessels, are also significantly correlated with cervical neoplasia. These features are irregular in size, shape, and arrangement, and the intercapillary distances of these features of abnormal epithelium are substantially greater and more dispersed than those of normal epithelium. The vessel features are automatically detected in the segmented image region. The vessel detection algorithm preferably uses a linear rotating structuring element (ROSE) and a morphological transformation to detect mosaicism, punctation, and atypical vessel patterns (as described in W. Li and A. Poirson, "Detection and characterization of abnormal vascular patterns in automated cervical image analysis," *Lecture Notes in Computer Science* 4292, 627, 2006, incorporated herein by reference). The following quantitative vessel structure features are preferably extracted for each image region: intercapillary distance between vessels, size of each vessel, and density of the vessels.

Diagnostic Image Classification

Given the statistical and quantitative features (mean, standard deviation, entropy and ratio for acetowhitening, and size, spacing and density for vessel structures) extracted from each image region, the tissues in these regions are classified as normal or abnormal using an automated image classification algorithm. The presently preferred embodiment of the invention preferably uses a classifier based on a CRF model incorporating the classification results of neighboring regions in a probabilistic manner (J. Lafferty, A. McCallum, and F. Pereira, "Conditional random fields: Probabilistic models for segmenting and labeling sequence data," *Proceedings of the International Conference on Machine Learning ICML*2001, 2001, incorporated herein by reference).

Probabilistic dependencies between neighboring regions are well modeled by random fields with the Markov property. Among such random field models, the Markov Random Field (MRF) and Hidden Markov Model (HMM) are simple and very popular. However, these models assume independent observations, an assumption which does not hold for cervical tissue. For example, and as mentioned previously in the Background Art section herein, the teaching in colposcopy textbooks (see B. S. Apgar, Brotzman, G. L. and Spitzer, M., "Colposcopy: Principles and Practice," W.B. Saunders Company, Philadelphia, 2002, incorporated herein by reference), states a high correlation between acetowhitening and mosaicism/punctation because the presence of both are highly indicative of cervical neoplasia. On the other hand, if a punctation or mosaic is not located in a field of acetowhite epithelium, they are unlikely to be associated with cervical neoplasia. Thus, the HMM and MRF models are not appropriate for our diagnostic image classification problem. Conversely, the CRF model is the preferred approach because it does not assume that the input features are statistically independent.

The CRF classifier design for the present invention is as follows:

Suppose that there are K image regions. Let $y_i$ denote the observed features for region i, $i \in \{1, \ldots, K\}$ and let $w_i \in \{0,1\}$ denote region i's classification label. The neighboring or adjacent regions of region i are then defined as those clusters sharing a cluster boundary with region i. In addition, $\partial_i$ and $w_{\partial_i}$ are the set of regions adjacent to region i and their classes, such that $w_{\partial_i} = \lfloor w_j \rfloor_{j \in \partial_i}$. Following the Hammersley-Clifford theorem (P. L. Dobrushin, "The description of a random field by means of conditional probabilities and conditions of its regularity," *Theory of Probability and its Applications* 13(2), pp. 197-224, 1968, incorporated herein by reference), the posterior probability distribution $$\tilde{p}_{W_i|W_{\partial_i},Y_i}(w_i|w_{\partial_i}, y_i)$$

can then be expressed according to $$\tilde{p}_{W_i|W_{\partial_i},Y_i}(w_i \mid w_{\partial_i}, y_i) = \frac{1}{Z} e^{-\frac{U_i(w_i|w_{\partial_i}, y_i)}{T}}, \quad (6)$$

where $$U_i(w_i \mid w_{\partial_i}, y_i) = V_{i,1}(w_i \mid y_i) + V_{i,2}(w_i \mid w_{\partial_i}), \quad (7)$$

$$V_{i,1}(w_i \mid y_i) = -\ln p_{W_i|Y_i}(w_i \mid y_i), \quad (8)$$

Figure 6:
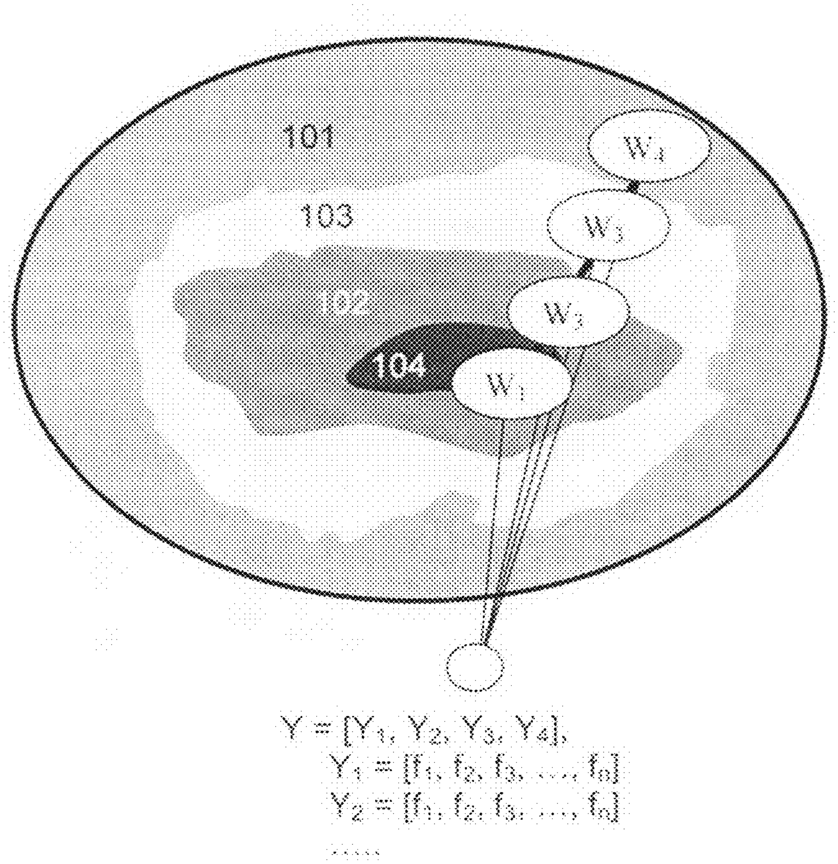
FIG. 6 illustrates the CRF (conditional random field) classifier design for a four cluster case ($W_1$, $W_2$, $W_3$, and $W_4$) with four different tissue types of squamous epithelium (101), columnar epithelium (102), transformation zone (103), and cervical os (104) utilizing feature functions ($Y_1$, $Y_2$, $Y_3$, and $Y_4$) for n different features $f_1$, $f_2$, $f_3$, . . . $f_n$.

-continued $$V_{i,2}(w_i \mid w_{\partial_i}) = \sum_{j \in \partial_i} g_i(w_i, w_j), \quad (9)$$

$$g_i(w_i, w_j) = \begin{cases} \alpha_i & \text{if } w_i = w_j \\ \beta_i & \text{if } w_i \neq w_j, \end{cases} \quad (10)$$

and T, $\alpha_i$, and $\beta_i$ are parameters, $$Z = \sum_{\forall y_i} e^{-\frac{U_i(w_i|w_{\partial_i}, y_i)}{T}} \quad (11)$$

is a normalization factor, and $p_{W_i|Y_i}(w_i|y_i)$ is the conditional probability distribution for the presence of cervical neoplasia in region i, ignoring information from neighboring regions. Here, capital letters represent random variables and the corresponding lower-case letters represent realizations of those random variables. For example, X is a random variable and x is a realization of X. FIG. 6 illustrates the CRF model of the current invention for a four cluster case ($W_1$, $W_2$, $W_3$, and $W_4$) with four different tissue types of squamous epithelium (101), columnar epithelium (102), transformation zone (103), and cervical os (104) utilizing feature functions ($Y_1$, $Y_2$, $Y_3$, and $Y_4$) for n different features $f_1$, $f_2$, $f_3$, . . . $f_n$.

The conditional probability distribution given only the diagnostic features, $p_{W_i|Y_i}(w_i|y_i)$, is determined from the ensemble results of a K-nearest neighbor (KNN) classifier and a linear discriminant analysis (LDA) classifier (as detailed in S. Y. Park, M. Follen, A. Milbourne, H. Rhodes, A. Malpica, N. MacKinnon, C. MacAulay, M. K. Markey, and R. Richards-Kortum, "Automated image analysis of digital colposcopy for the detection of cervical neoplasia," *Journal of Biomedical Optics* 13, 014029, 2008, incorporated herein by reference).

The maximum a posteriori (MAP) estimation is applied to determine the parameters of the posterior probability distribution described by Equation (6). The MAP estimate $w_i^{MAP}$ for $W_i$ is defined as:

$$w_i^{MAP} = \underset{w_i}{\operatorname{argmax}} \tilde{p}_{W_i|W_{\partial_i},Y_i}(w_i \mid w_{\partial_i}^{MAP}, y_i) \quad (12)$$

where $$w_{\partial_i}^{MAP} = [w_j^{MAP}]_{j \in \partial_i}. \quad (13)$$

Using the estimated posterior probability distribution, image regions are classified as normal or abnormal. This binary (normal versus abnormal) classification is performed using the Pareto optimal threshold (J. P. Aubin and S. Wilson, *Optima and Equilibria: An Introduction to Nonlinear Analysis*, Springer-Verlag, 1993, incorporated herein by reference) for the probability of cervical neoplasia obtained by Receiver Operating Characteristic (ROC) analysis. The ROC analysis uses leave-one-patient-out cross-validation (as described in R. Kohavi, "A study of cross-validation and bootstrap for accuracy estimation and model selection," *International Joint Conference on Artificial Intelligence* 14, pp. 1137-1145, 1995, incorporated herein by reference) to assess the diagnostic performance of the classifier.

Performance Evaluation

Approach

Sensitivity and specificity are widely used statistical measures for assessing the performance of diagnostic algorithms. However, cervical image analysis must apply these measures in a meaningful way, because a useful diagnostic algorithm should be able to locate abnormal tissue regions on the cervix rather than provide a single diagnosis for an entire image. As discussed previously in the Background Art section, it is clinically important to accurately locate the abnormal region in addition to providing an overall diagnosis. In order to address this problem, the preferred embodiment of the invention utilizes a novel window-based approach for determining the sensitivity and specificity of the detection and diagnosis algorithms. This window-based approach is implemented as follows:

The cervical reflectance image is first portioned into disjointed windows (windows which do not overlap). The classification result for each window is then compared to the histopathology ground truth annotations of the corresponding window in the histopathology image. If both results are positive, the number of true positives for the subject is increased. If both results are negative, the number of true negatives is increased. Lastly, if two results do not match, the numbers of either false positives or false negatives are increased.

Determining the appropriate window size is a design challenge with this window-based method. As the window size increases, the sensitivity increases and the specificity decreases. A large window size provides a large region for assessment, and the probability that positive diagnosis matches the histopathology becomes high; conversely the probability for negative diagnosis becomes low. Therefore, the desirable window size is just large enough to cover image registration errors between the cervical RGB image and the histopathology image. This window size yields a good correspondence between the algorithm's diagnostic results and the histopathology. As part of the process of maintaining the orientation of the LEEP specimen and correlating the histopathology annotations the cervical reflectance images (as described in the co-pending, commonly assigned U.S. patent application Ser. No. 12/587,614 for "Process for preserving 3D orientation to allowing registering histopathological diagnoses of tissue to images of that tissue", filed Oct. 9, 2008, incorporated herein by reference), a misalignment of up to 1-2 mm between the cervical RGB images and the histopathology images can be accommodated. Therefore, the window size is varied from 5×5 pixels to 50×50 pixels, corresponding to 200 μm to 2 mm of registration error. For each window size, the sensitivity and specificity are calculated. ROC curve analysis is then performed and the Pareto optimal threshold is determined.

Histopathology Ground Truth

To compare the performance of the diagnosis framework to that of an expert colposcopist, the window-based performance measure was applied to both the expert-colposcopy annotated images and the diagnostic results of the described algorithm. In both cases, histopathology was used as ground truth.

The pre-acetic acid and post-acetic acid cervical reflectance images from 48 subjects were analyzed. The histopathology showed 7 subjects with carcinoma in situ (15%), 40 patients with high grade (83%), and 1 patient with low grade (2%). Among the 47 subjects with high grade or carcinoma, colposcopy annotations revealed 11 subjects with mosaicism, 24 with punctation, and 8 with atypical vessel patterns. The acetowhitening feature was present in all high-grade subjects.

Figure 7A:
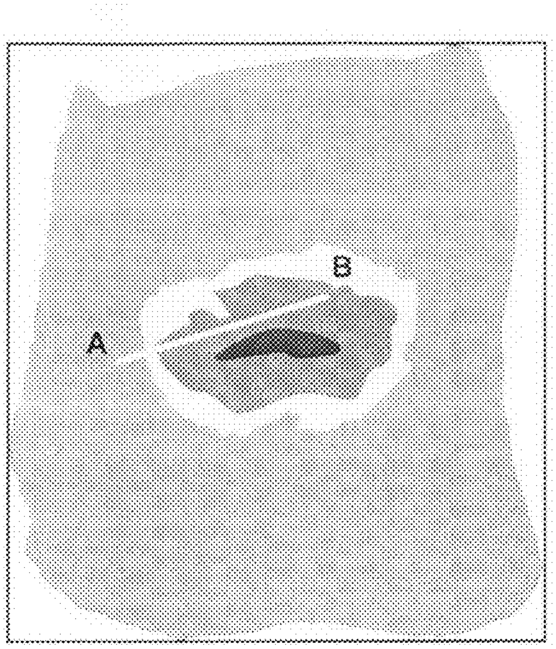
FIG. 7(*a*) illustrates a polarized white light cervical image with points A to B denoting the position of a histoplathology slide from a loop electrosurgical excision procedure (LEEP) from a cervix.
Figure 7B:
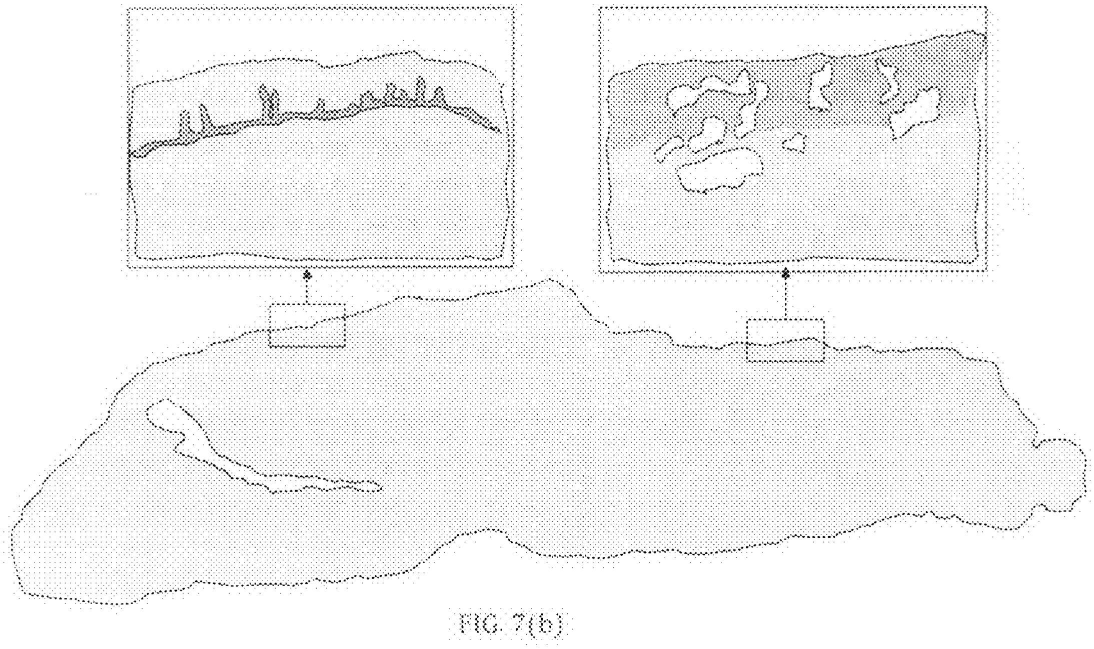

FIG. 7(*a*) illustrates a white light reflectance image of a cervix. LEEP specimen cross-sectioning between point A (squamous epithelium) and point B (columnar epithelium) in FIG. 7(*a*) is shown in FIG. 7(*b*). As shown in the enlarged histology slide images in FIG. 7(*b*), the tissue structure varies significantly with tissue type.

Diagnostic Feature Extraction and Classification

As a first test of performance of the present invention, an analysis was performed that verified the previously reported observations that columnar tissue is spectroscopically distinct from the adjacent squamous tissue (as discussed by J. Mirkovic, C. Lau, S. McGee, C. C. Yu, J. Nazemi, L. Galindo, V. Feng, T. Darragh, A. de Las Morenas, and C. Crum, "Effect of anatomy on spectroscopic detection of cervical dysplasia," *Journal of Biomedical Optics* 14, p. 044021, 2009, incorporated herein by reference), and that the acetowhite response curves have different decays in squamous and columnar tissue (as discussed by I. M. Orfanoudaki, G. C. Themelis, S. K. Sifakis, D. H. Fragouli, J. G. Panayiotides, E. M. Vazgiouraki, and E. E. Koumantakis, "A clinical study of optical biopsy of the uterine cervix using a multispectral imaging system," *Gynecologic Oncology* 96(1), pp. 119-131, 2005, incorporated herein by reference).

Figure 8A:
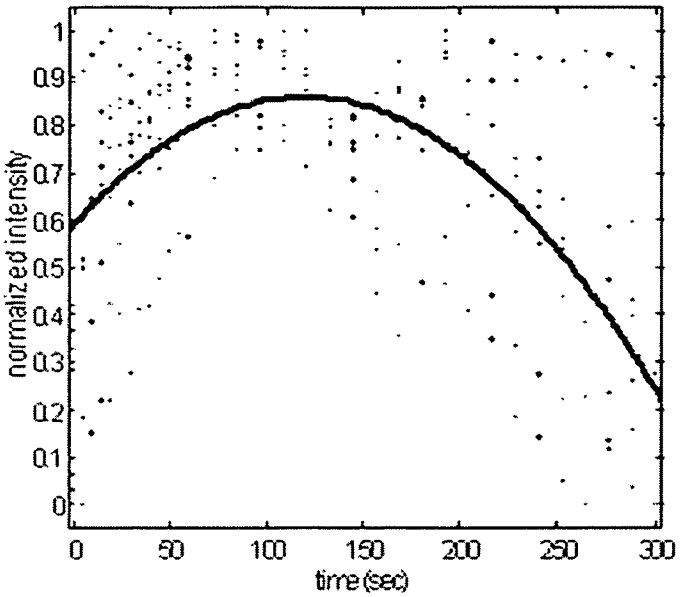
FIG. 8(*a*) shows the acetowhite signal decay curves from squamous tissue, and FIG. 8(*b*) shows the acetowhite signal decay curves from columnar epithelium tissue.
Figure 8B:
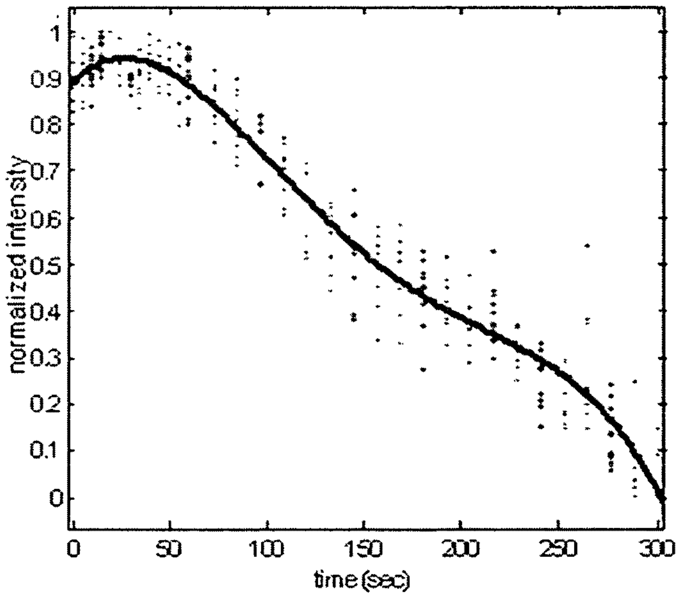
Figure 9A:
FIG. 9(*a*) compares the results of the disclosed algorithm for a first subject with corresponding colposcopy annotations shown in FIG. 9(*c*) performed by an expert colposcopist in extracting acetowhitening areas, and FIG. 9(*b*) compares the results of the present invention for a second subject with corresponding colposcopy annotations shown in FIG. 9(*d*) performed by an expert colposcopist in extracting acetowhitening areas.
Figure 9B:
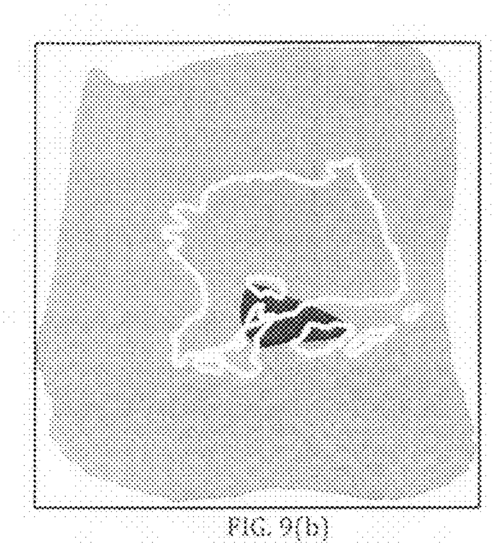
Figure 9C:
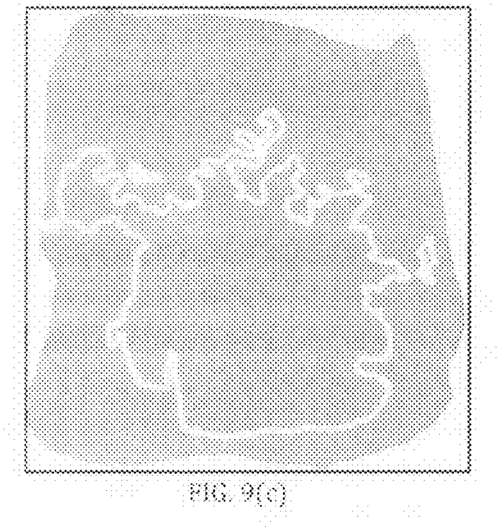
Figure 9D:
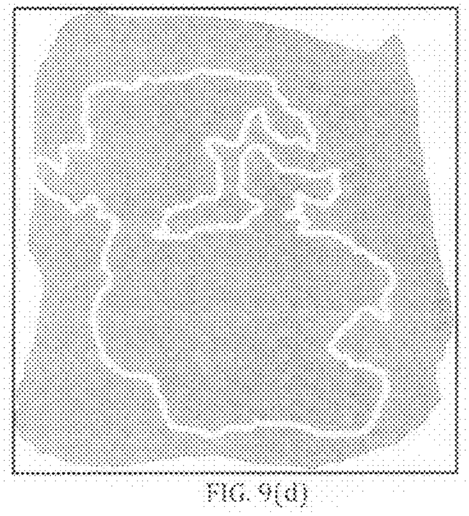

As discussed in the "Instrumentation and Data-Data" section herein, a sequence of polarized cervical reflectance images was captured after the application of acetic acid on the cervix every ten seconds for five minutes. 20×20 pixel windows were sampled from the acetowhite colposcopically annotated regions of the acquired images in the squamous and columnar epithelium tissue areas. For each window, the mean of the intensity ratio of the green and red channels was calculated. FIG. 8 shows the acetowhite signal decay curves from the squamous epithelium (FIG. 8(*a*)) and the columnar epithelium (FIG. 8(*b*)). It can clearly be seen that the green to red intensity ratio varies with time. In addition, the signal acquired from the columnar epithelium tissue area decays more rapidly than the signal from the squamous tissue area. As exemplified in this analysis, there are significant differences in the optical properties of different tissue types. The performance of diagnostic algorithms can, thus, be improved by explicitly incorporating this observation.

As a second test of the performance of the present invention, the acetowhite extraction results were compared to annotations performed by an expert colposcopist. The result of this analysis is illustrated in FIG. 9 for two different subjects (FIG. 9(*a*)-(*c*) and FIG. 9(*b*)-(*d*), respectively) and, as can be seen, the extraction result and the annotations provide similar results.

Figures 10A, 10B, 10C:
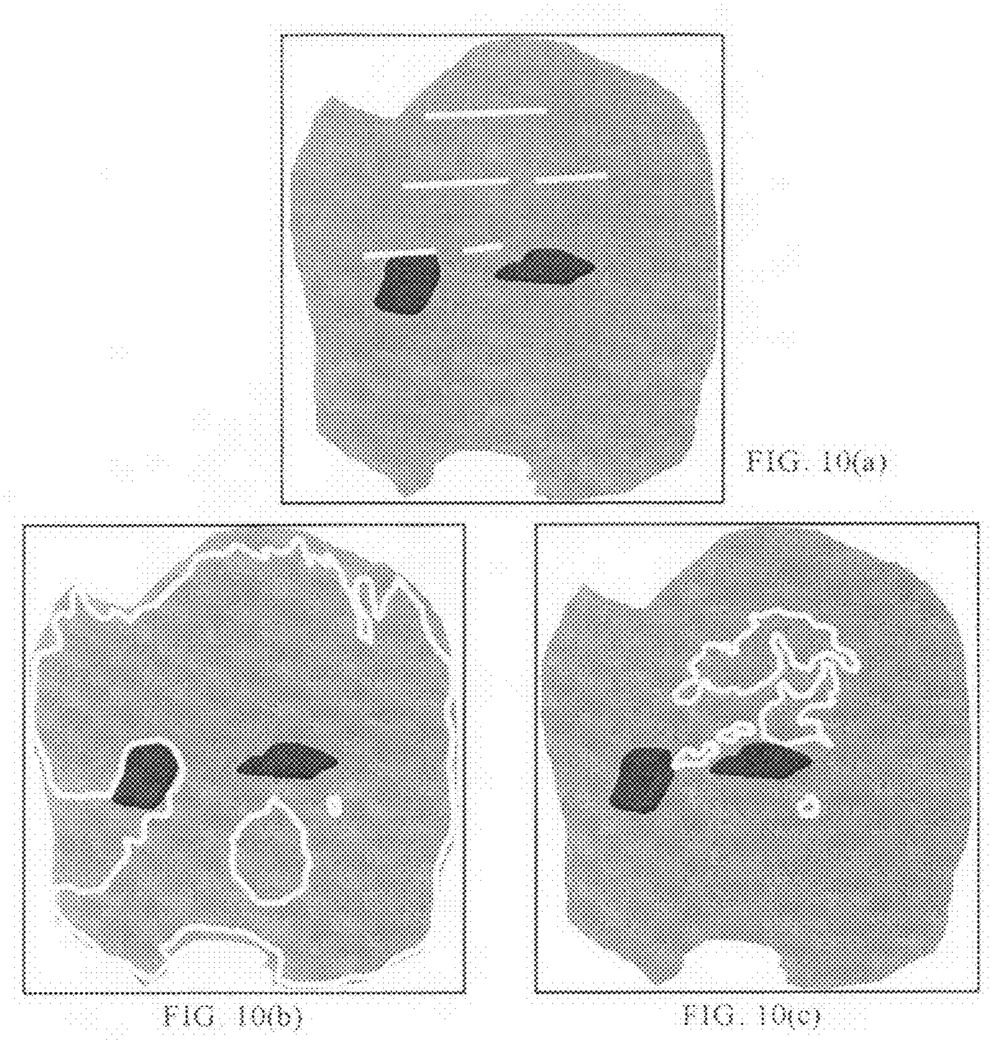
FIGS. 10(*a*) and 11(*a*) show the histopathology ground truth annotations for two different subjects overlaid on the cervical images. Areas with high grade neoplasia or carcinoma in situ areas are shown as white colored lines.
Figure 11A:
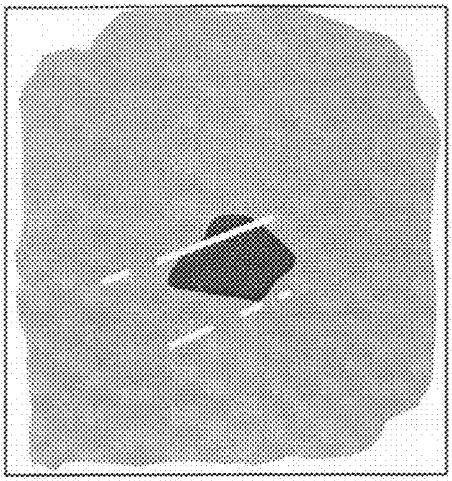
Figure 11B:
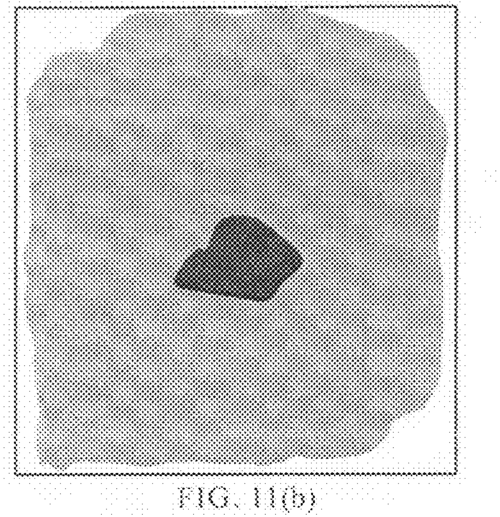
Figure 11C:
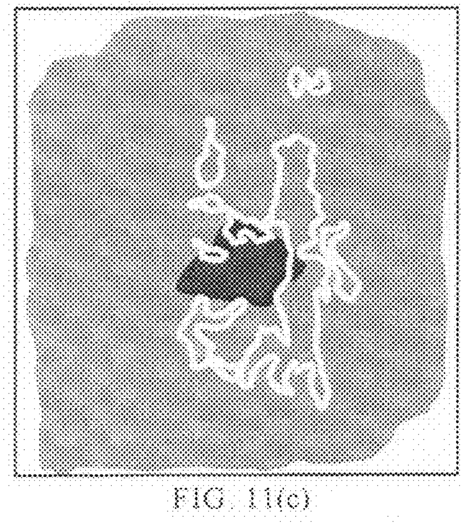

As a follow up to the second test, a third comparison test shows that the present invention outperforms colposcopy annotations for many subjects. Two types of outperforming cases were identified; in the first type, the abnormal area from the colposcopy annotation is too large, and in the second type the colposcopy annotation does not recognize the abnormal area. FIG. 10 and FIG. 11 exemplify the two outperforming cases by showing the colposcopy annotations and the diagnostic results of the disclosed diagnostic image analysis algorithm for two subjects, with histopathology as the ground truth. FIGS. 10(*a*) and 11(*a*) show the histopathology annotations for the two subjects, with the corresponding colposcopy annotations and diagnostic image analysis algorithm results shown in FIG. 10(*b*), 11(*c*) and FIG. 10(*b*), (*c*), respectively.

The first subject represents the first type of outperforming case. As seen in FIG. 10(*b*), the colposcopy annotation suggests an abnormal region largely corresponding to the normal area in histopathology. This results in high sensitivity but low specificity for the colposcopy annotation. On the other hand, the abnormal area detected by the proposed disclosed diagnostic image analysis algorithm, as shown on FIG. 10(*c*) closely matches that of the histopathology image of FIG. 11(*a*). This results in a similar level of sensitivity to the colposcopy annotation but with a much higher specificity.

The second subject is an example of the second outperforming case. For this subject, the colposcopy annotation (FIG. 11(*b*)) shows no abnormal region at all, while the disclosed diagnostic image analysis algorithm (FIG. 11(*c*)) outputs abnormal regions which closely match those from the histopathology image (FIG. 11(*a*)).

Figure 12A:
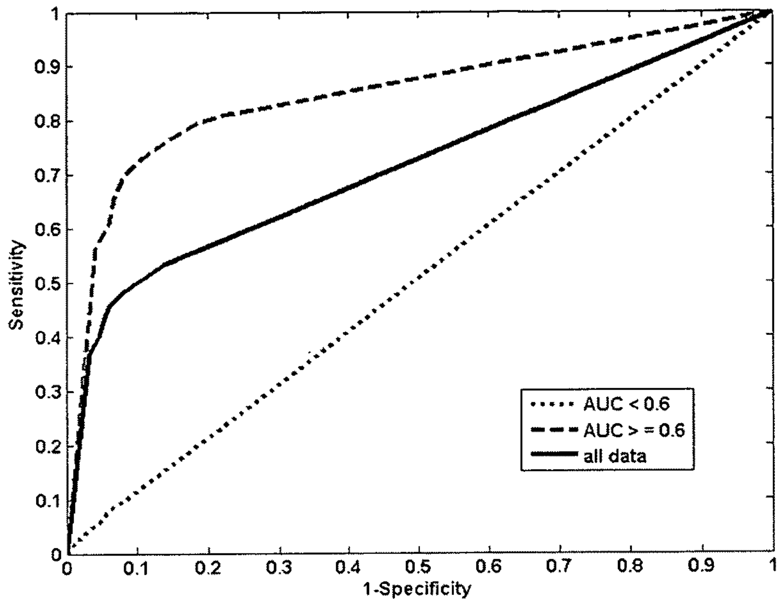
FIG. 12 display the receiver operator characteristics (ROC) curves of the diagnostic results from (*a*) the expert colposcopists and (*b*) the disclosed diagnostic image analysis framework.
Figure 12B:
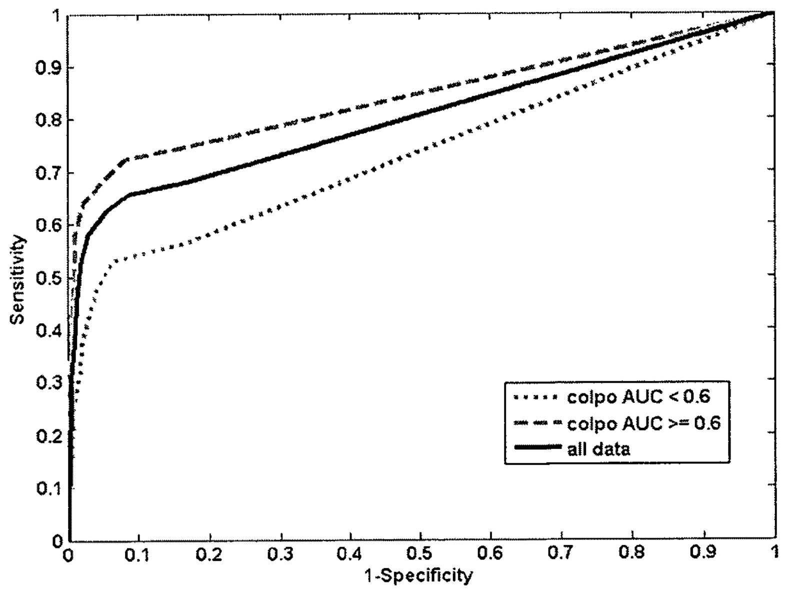

As a fourth and final test, the result of the window-based performance measure and ROC curve analysis for colposcopy annotations and the disclosed diagnostic image analysis algorithm is displayed in FIG. 12. The ROC curves are generated for the colposcopy annotations (FIG. 12(*a*) and the disclosed diagnostic image analysis algorithm (FIG. 12(*b*)) using window-based assessment with varying window size are presented. All ROC curves use the histopathology annotations and ground truth. The ROC curves are for all 48 subjects, averaged from the ROC curves of the individual subjects. In addition, the ROC curves represented by the solid line, the dashed line, and the dotted line are for all subjects, for subjects with high Area Under the ROC Curve (AUC)($\geqq$0.6), and for subjects with low AUC (<0.6), respectively.

The diagnostic potential of the disclosed diagnostic image analysis algorithm is demonstrated with an average sensitivity of 70% and specificity of 80% in detecting neoplastic areas. This performance compares favorably with the 60% sensitivity and 70% specificity of the colposcopy annotations. As shown in the FIG. 12(*a*) and (*b*), respectively, the disclosed image analysis algorithm's diagnostic performance is comparable to that of the colposcopy annotations. Moreover, for the patients with low AUC, the algorithm correctly identifies abnormal regions which are missed by the colposcopy annotations.

Notably, this performance differs from previously reported subject-based analyses with 87-96% sensitivity and 34-85% specificity for colposcopy annotations (see for example M. F. Mitchell, D. Schottenfeld, G. Tortolero-Luna, S. B. Cantor, and R. Richards-Kortum, "Colposcopy for the diagnosis of squamous intraepithelial lesions: a meta-analysis," *Obstetrics & Gynecology* 91(4), p. 626, 1998; J. L. Benedet, G. H. Anderson, J. P. Matisic, and D. M. Miller, "A quality-control program for colposcopic practice," *Obstetrics & Gynecology* 78(5), p. 872, 1991; and L. Seshadri, P. Jairaj, and H. Krishnaswami, "Colposcopy in the diagnosis of cervical neoplasia," *Indian Journal of Cancer* 27(3), p. 180, 1990, incorporated herein by reference). This difference can be attributed to the fact that these previously reported patient-based analyses do not take into account the issue of locating the abnormal regions in the images. The patient-based performance assessment scheme is essentially the same as the disclosed window-based approach if the window size is set large enough to contain the entire image. Using such a large window size covering the entire cervix obviously yields high sensitivity and low specificity, as discussed previously in "Performance Analysis-Approach" section herein.

CONCLUSION

In summary, the disclosed automated diagnostic approach can support or potentially replace conventional colposcopy, allowing a less trained provider to identify the diagnostically significant features and to quantitatively assess the margin of neoplastic lesions at a level on par with an expert colposcopist. In the clinic, this technique may allow LEEP to be performed in a more objective manner, addressing differences in skill levels between practitioners. Furthermore, the disclosed invention may provide both a higher standard of care and a more cost effective screening solution in low-resource settings, by reducing the need for extensive provider training and expertise. This would result in earlier cervical cancer detection and prevention in developing countries.

INDUSTRIAL APPLICATIONS

This invention provides the means to detect and diagnose cervical cancerous lesions. The method described may also be suitable for other tissue diagnosis instruments and other imaging systems that are designed to detect and diagnose cancerous tissue.

What is claimed is:

1. A process for detection and diagnosis of cancer in tissues, comprising:
- acquiring polarized and non-polarized images of said tissues;
- normalizing said images to account for color and spatial variations;
- registering said images to correct for tissue deformation;
- generating an anatomical features map from said images using color and texture information;
- identifying regions in said images of different tissue types based on said anatomical features map, whereby each region has only one tissue type;
- segmenting sub-regions within each region that are homogeneous in color and intensity;
- extracting diagnostically relevant features from each of said sub-regions, wherein said diagnostically relevant features are selected from the group consisting of acetowhitening and abnormal blood vessel features; and
- classifying said sub-regions as normal or abnormal based on said extracted diagnostically relevant features in said sub-regions and probabilistic dependencies based on classification of neighboring regions;
- wherein said extracting diagnostically relevant features step for acetowhitening is performed by calculating mean, standard deviation, entropy and ratios between different color channels of said images of said tissue.

2. A process according to claim 1, wherein said extracting diagnostically relevant features step is performed for abnormal vessel features by applying a linear rotating structuring element and a morphological transformation to automatically detect mosaicism, punctation, and atypical vessel patterns by extracting intercapillary distance between vessels, size of each vessel, and density of vessels.

3. A process according to claim 1, further comprising: automatically classifying tissues in each sub-region as normal or abnormal using a conditional random field classifier that incorporates probabilistic dependencies on classification of neighboring sub-regions.

4. A process according to claim 1, wherein said tissues are cervical tissues and said identifying step identifies said tissue types as squamous epithelium, columnar epithelium, cervical os, and transformation zone.

5. A process according to claim 1, wherein said images are red, green and blue visible light images.

6. A process according to claim 1, wherein said images are selected from the group consisting of pre-acetic acid images, post-acetic acid images, time course acetowhite images and reflectance and fluorescence images.

* * * * *